US00PP27420P3

(12) United States Plant Patent
Cripps

(10) Patent No.: US PP27,420 P3
(45) Date of Patent: Nov. 29, 2016

(54) APPLE TREE NAMED 'ANABP 01'

(50) Latin Name: ***Malus domestica* Borkh.**
Varietal Denomination: ANABP 01

(71) Applicant: Western Australia Agriculture Authority Department of Agriculture and Food, Bentley, Western Australia (AU)

(72) Inventor: John E. Cripps, Floreat (AU)

(73) Assignee: Western Australian Agriculture Authority, Bentley, Western Australia ( * ) Notice: Subject to any disclaimer, the term of this patent is extended or adjusted under 35 U.S.C. 154(b) by 175 days.

(21) Appl. No.: 14/121,047

(22) Filed: Jul. 23, 2014

(65) Prior Publication Data

US 2016/0029527 P1 Jan. 28, 2016

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Keith Robinson
(74) *Attorney, Agent, or Firm* — Michelle Bos Legal LLC

(57) ABSTRACT

'ANABP 01' is a new and distinct apple variety (*Malus domestica* Borkh.) notable for its attractive dark purple red skin color, excellent flavor and texture, attractive size and shape, and consistent cropping characteristics.

6 Drawing Sheets

Latin name: *Malus domestica* Borkh.
Variety denomination: 'ANABP 01'.

BACKGROUND OF THE VARIETY

'ANABP 01' originated as a seedling produced from a controlled cross performed in a sexual breeding program conducted by the State of Western Australia at Stoneville Research Station, Western Australia in the spring of 1992. It was bred using conventional breeding techniques. 'ANABP 01' is a cross between female parent 'Cripps-Two' (U.S. Plant Pat. No. 8,477; also known as 'Cripps Red') and male parent 'Tenroy' Gala (U.S. Plant Pat. No. 4,121; also known as 'Royal Gala'). 'ANABP 01' was first asexually propagated, by grafting onto rootstocks, at Manjimup Horticultural Research Institute, Manjimup, Western Australia in July 1999, and has since been shown to remain true to type over successive asexually propagated generations.

The fruit of 'ANABP 01' is distinguishable from its parents by the hue of its overcolor at maturity. 'ANABP 01' has very dark purple red skin, as compared to the pink over yellow-green of 'Cripps-Two' and the striped red over yellow of 'Tenroy.' The fruit of 'ANABP 01' is further distinguished from 'Cripps-Two' by its somewhat larger size, the presence of bloom on its skin, and its thicker stalk and earlier harvest maturity. The leaf petiole of 'ANABP 01' is shorter than that of 'Cripps-Two.'

ANABP 01 was selected for its desirable fruit characteristics, including:

appealing and distinctive color
excellent flavor and texture
attractive size and shape
consistent cropping behavior

BRIEF DESCRIPTION OF THE PHOTOGRAPHS

Figure 1:
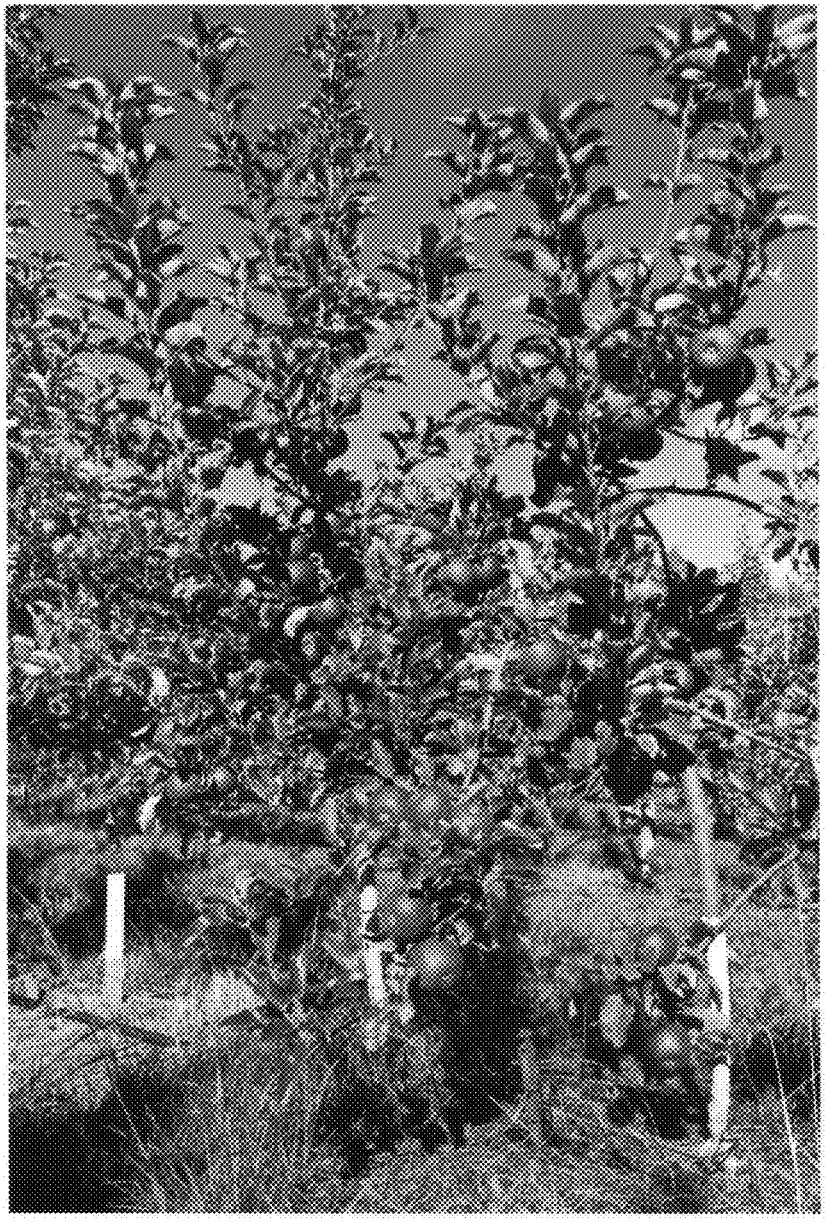

FIG. 1 'ANABP 01' fruit on young tree prior to harvest (image taken 7 Apr. 2010).

Figure 2:
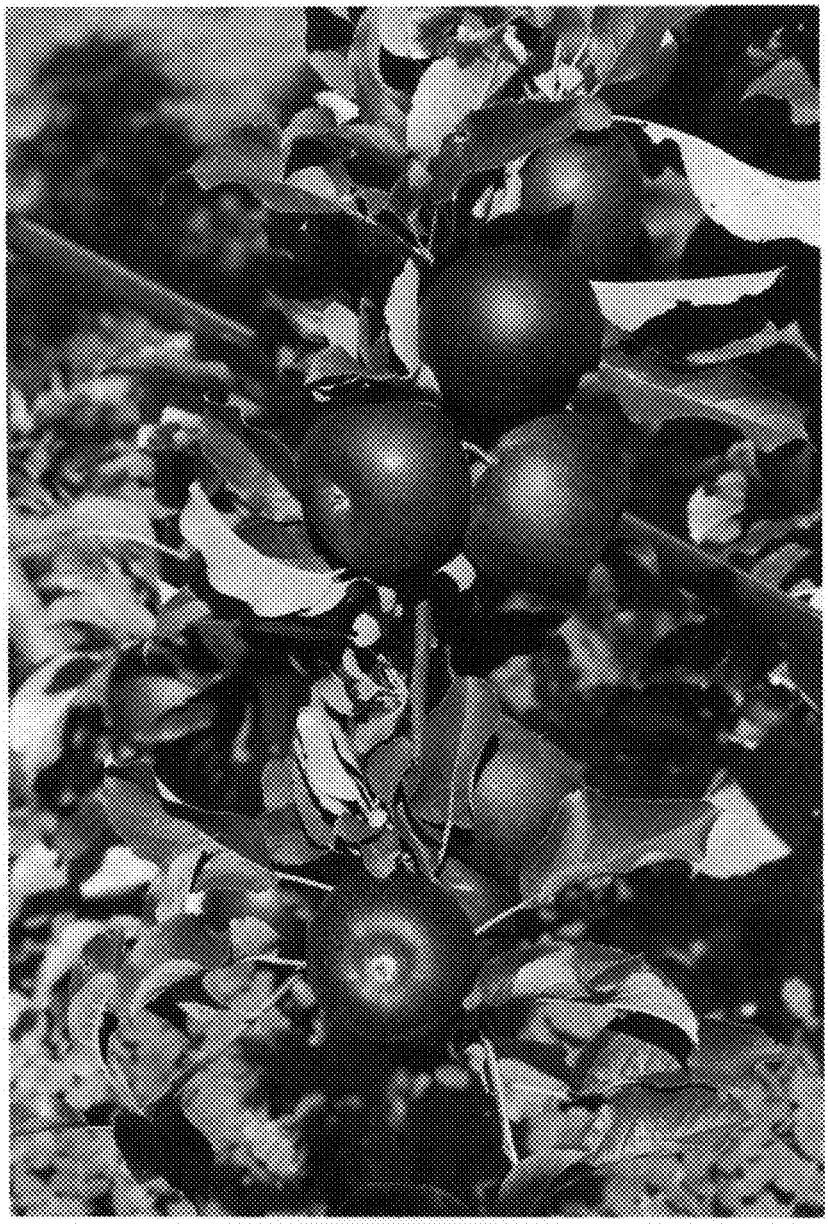

FIG. 2 'ANABP 01' fruit hanging on tree limb (image taken 29 Apr. 2010).

Figure 3:
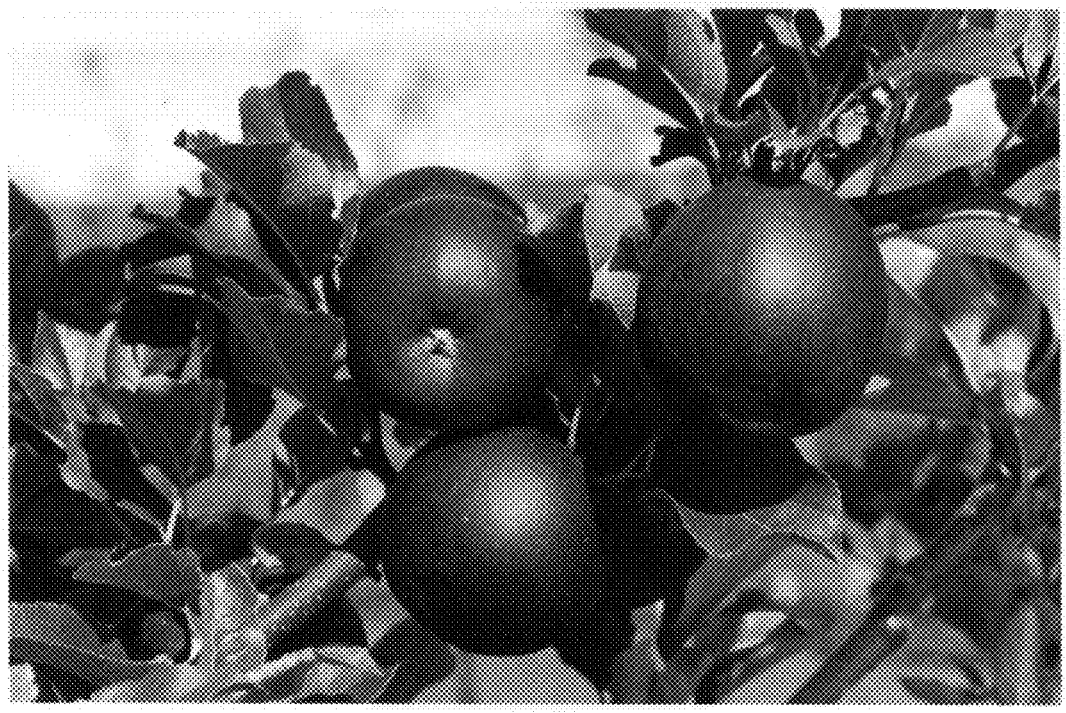

FIG. 3 'ANABP 01' fruit on tree (Image taken 29 Apr. 2010).

Figure 4:
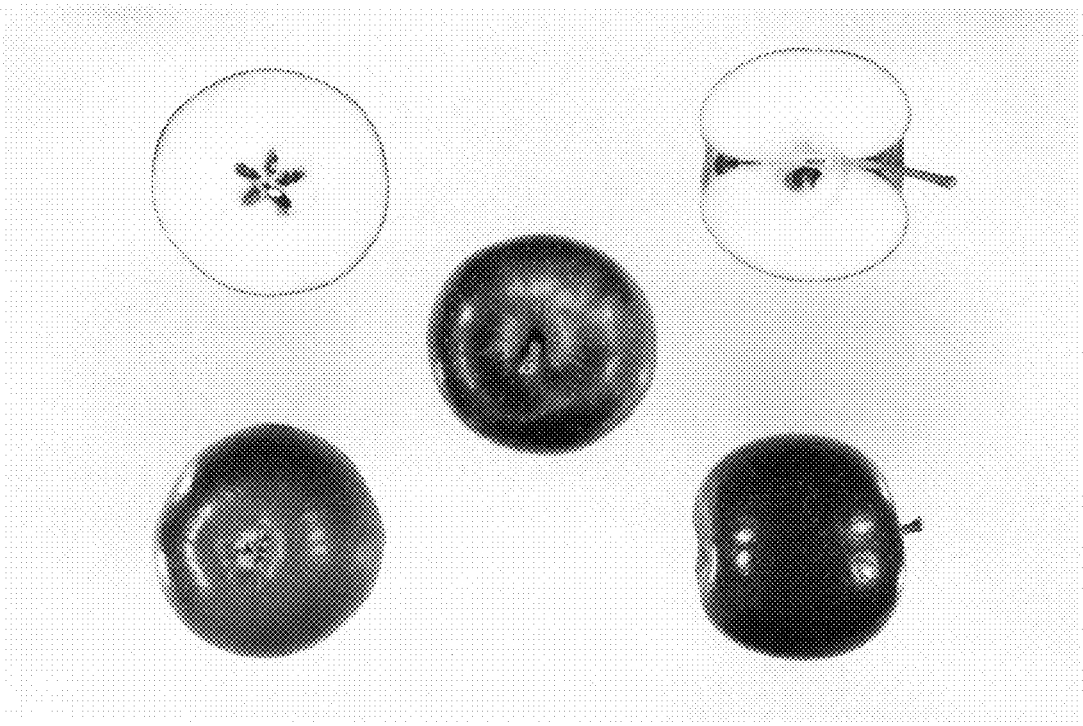

FIG. 4 'ANABP 01' showing fruit shape and skin color (image taken 28 Apr. 2010).

Figure 5:
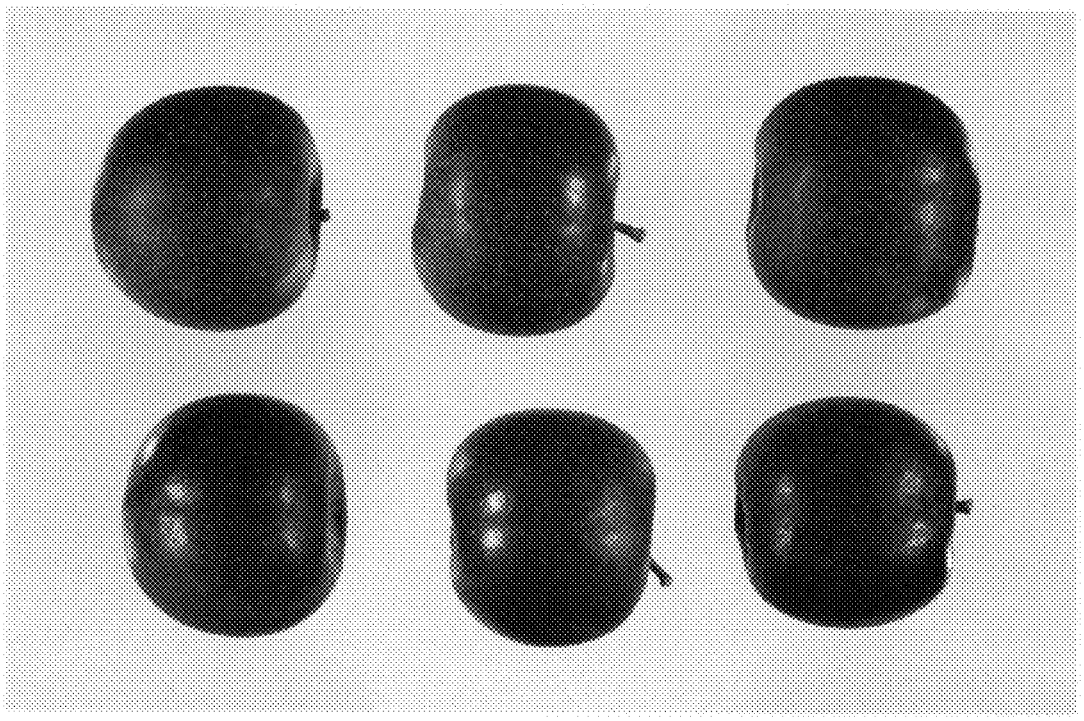

FIG. 5 'ANABP 01' showing side on view of fruit (image taken 28 Apr. 2010).

Figure 6:
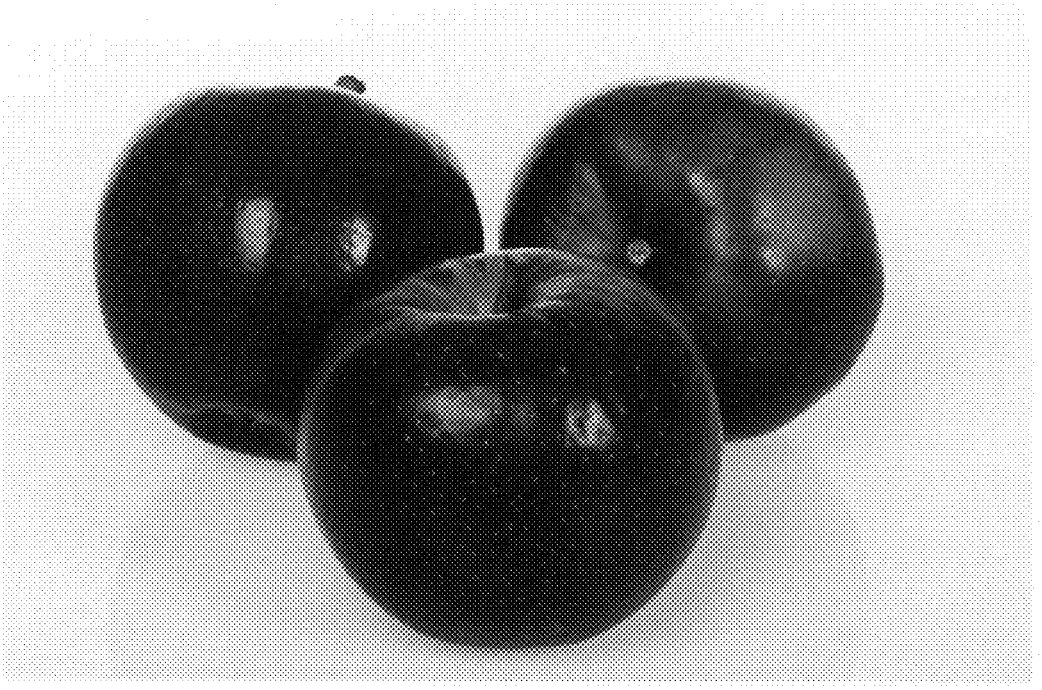

FIG. 6 'ANABP 01' fruit showing lenticel prominence (image taken 28 Apr. 2010).

DETAILED BOTANICAL DESCRIPTION OF THE VARIETY

The following-detailed botanical description is based on observations made during the 2009/2010 growing season of four year old trees growing at Manjimup, Western Australia. The described trees were planted in 2006 on 'MM 106' rootstock (not patented), and grown on a central leader training system. All colors are described according to The Royal Horticultural Society Colour Chart (5th ed., 2007). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Medium — similar to 'Golden Delicious' (not patented).
*Type.*—Ramified.
*Habit.*—Spreading — similar to 'Jonagold' (not patented).
*Height.*—2.9 m.
*Diameter.*—1.3 m.

*Trunk diameter* (*at* 30 *cm above ground level*).—3.7 cm.
*Trunk girth* (*at* 30 *cm above ground level*).—12.2 cm.
*Bark texture.*—Smooth.
*Bark color.*—Greyed brown 199B to greyed brown 165C.
*Trunk lenticel diameter.*—1.7 mm.
*Trunk lenticel color.*—Greyed white 156B.

Branch (fruiting branches located at around 1 m above the graft union):
*Length.*—134.3 cm (3 year old branches between 1 m and 1.5 m from the ground and directly off the central leader).
*Diameter.*—16 mm.
*Crotch angle.*—40° to 85°, average 69°.
*Color* (*sunny side*).—Greyed brown 199B.
*Branch lenticel diameter.*—1.4 mm.
*Branch lenticel color.*—Greyed white 156B.
*Branch lenticel quantity.*—6.4 per $cm^2$.

One-year-old shoot:
*Length.*—46.6 cm.
*Color.*—Greyed purple N186C.
*Pubescence.*—Weak — similar to 'Golden Delicious'.
*Thickness.*—Thick, 7.0 mm.
*Internode length.*—Medium, 28.8 mm.
*Shoot lenticel diameter.*—1.2 mm.
*Shoot lenticel quantity.*—6.7 per $cm^2$.
*Shoot lenticel color.*—Greyed green 196C.

Winter hardiness:
*Hardiness.*—Not known.
*Chilling requirement.*—Medium, approximately 400 to 500 hours below 7.2 degrees Celsius.

Flower buds:
*Flower clusters per spur.*—4.2.
*Shape of dormant flower bud* (*spur wood*).—Conical with pointed apex.
*Length of dormant flower bud* (*spur wood*).—9.5 mm.
*Diameter of dormant flower bud* (*spur wood*).—4.4 mm.
*Color.*—Greyed purple 187A.

Flowers:
*Color* (*balloon stage*).—Dark pink — ranges between red purple 59D and 64D, depending on balloon expansion.
*Diameter of open flower.*—Large, 51.2 mm (measured with petals pressed into horizontal position).
*Relative position of petal margin.*—Intermediate (generally just touching or slightly overlapping adjacent petals).
*Depth.*—20.6 mm (measured from base of sepals to highest point of flower).
*Quantity per cluster.*—6.0.
*Quantity per spur.*—14.3.

Petals:
*Quantity per flower.*—5.
*Shape.*—Ovate.
*Length.*—22.2 mm.
*Width.*—15.4 mm.
*Apex.*—Rounded.
*Base.*—Triangular to slightly rounded.
*Margin.*—Smooth.
*Color of upper surface.*—Red purple N66D (darkest point of color measured).
*Color of lower surface.*—Red purple group 62B (darkest point of color measured).

Pistils:
*Length.*—15.7 mm.
*Color.*—Yellow green 146D.

Anthers:
*Quantity.*—17.9 mm.
*Length.*—1.85 mm.
*Is pollen produced?.*—Yes.
*Color of pollen.*—Yellow 12C.
*Color of anthers prior to dehiscence.*—Yellow 11B.

Stigma:
*Length.*—1.3 mm.
*Width.*—0.3 mm.
*Color.*—Yellow green 145B.

Style:
*Length.*—9.9 mm.
*Color.*—Yellow green 146D.

Ovary:
*Length.*—4.9 mm.
*Color—external.*—Greyed green 191C.
*Color—internal, cut horizontally.*—Yellow green 146B.

Blooming:
*Date of first bloom.*—First bloom occurs mid- to late October in Manjimup (Oct. 31, 2005 and Oct. 15, 2009).
*Date of full bloom.*—Full bloom occurs from late October to early November in Manjimup (Nov. 8, 2005 and Oct. 28, 2009).

Pedicel:
*Length.*—27.6 mm.
*Diameter.*—1.3 mm.
*Color.*—Yellow green 146C.

Sepals:
*Quantity.*—5.
*Color.*—Yellow green 146D.
*Length.*—7.4 mm.
*Shape.*—Long, narrow triangular with pointed apex.

Leaves:
*Shape.*—Broad elliptic.
*Length* (*petiole not included*).—Short to medium, 87.8 mm.
*Width.*—Narrow to medium, 52.0 mm.
*Length/width ratio.*—Medium, 1.7:1.
*Leaf midvein width.*—1.0 mm (measured at mid-point of the leaf blade).
*Blade margin.*—Serrate.
*Apex.*—Mucronate.
*Base shape.*—Rounded.
*Coloration of top surface.*—Green N137B.
*Coloration of bottom surface.*—Yellow green 148B.
*Attitude in relation to shoot.*—Upward.

Petiole:
*Length.*—Short, 27.6 mm.
*Diameter.*—1.5 mm (measured at the mid-point of the petiole).
*Color—upper surface, pubescence removed.*—Greyed purple 187B.
*Color—lower surface, pubescence removed.*—Greyed purple 187C.

Fruit:
*Quantity per cluster.*—Light to moderate thinning was carried out to leave 1 to 2 fruits per cluster.
*Size.*—Medium to large, height 65.4 mm, diameter 79.3 mm.
*Weight.*—205.3 g.

*Ratio of height/width.*—Small, 0.82 mm.
*General shape in profile.*—Obloid.
*Position of maximum diameter.*—Near the center.
*Ribbing.*—Moderate.
*Crowning at calyx end.*—Moderate.
*Size of eye.*—Medium to large, average diameter 9.6 mm.
*Length of sepal.*—Short to medium, 4.2 mm.
*Depth of eye basin.*—Shallow, 5.2 mm.
*Width of eye basin.*—Medium to broad, 29.7 mm.
*Length of stalk.*—Short to medium, 19.9 mm.
*Thickness of stalk.*—Thick, 3.2 mm.
*Width of stalk cavity.*—Medium, 34.5 mm.
*Depth of stalk cavity.*—Medium, 11.3 mm.
*Size of lenticels.*—Small to medium, 0.7 mm.
*Number of lenticels.*—Many to very many, 9.8 per $cm^2$.
*Bloom of skin.*—Moderate.
*Greasiness of skin.*—Moderate.
*Background color of skin.*—Yellow/green to yellow; varies on maturity.
*Over color of skin.*—Purple N77.
*Amount of over color.*—Large to very large, 95% to 100%.
*Intensity of over color.*—Very dark.
*Pattern of over color.*—Solid flush.
*Flesh texture.*—Firm, average pressure 9.7 Kg/cm2 (Apr. 21, 2010).
*Juiciness.*—Moderate, 62.3% juice in flesh.
*Brix.*—Generally ranges between 11% and 16% TSS, but is dependent on the season and maturity at sampling (sample measured at 13.6% on Apr. 21, 2010).
*Flesh color.*—White 155B.
*Stem color.*—Greyed orange 165B.

Seeds:
*Quantity per fruit.*—9.6; seed numbers vary depending on pollination.
*Length.*—8.6 mm.
*Shape.*—Obovate.
*Color.*—Greyed orange 166A when moist.

Harvest:
*Harvest yield.*—Varies with tree maturity, rootstock, and other factors; yield of 56 tonnes/hectare recorded for 6-year-old trees on M26 rootstock at Donnybrook, Western Australia in 2013.
*Harvest date range.*—Harvest range is late to very late, after 'Granny Smith' (not patented) and before 'Cripps Pink' (U.S. Plant Pat. No. 7,880); Mid- to late April at Manjimup, Western Australia (2010 harvest took place between April 20th and April 30th).

Diseases/pests:
*Resistance.*—None noted.
*Susceptibility.*—None noted.

Market use: Fresh.

I claim:

1. A new and distinct apple tree substantially as described and illustrated herein.

* * * * *